United States Patent
Vernice

[11] Patent Number: 6,117,419
[45] Date of Patent: *Sep. 12, 2000

[54] DELIVERY SYSTEM FOR OIL SOLUBLE ACTIVES IN COSMETIC/PERSONAL CARE PRODUCTS

[76] Inventor: Joseph James Vernice, 80 Parkview Dr., Shirley, N.Y. 11967

[ * ] Notice: This patent issued on a continued prosecution application filed under 37 CFR 1.53(d), and is subject to the twenty year patent term provisions of 35 U.S.C. 154(a)(2).

[21] Appl. No.: 08/714,247

[22] Filed: Sep. 16, 1996

[51] Int. Cl.⁷ ...................................................... A61K 9/10
[52] U.S. Cl. .................... 424/70.1; 424/70.6; 424/70.12; 424/400; 424/401; 424/484; 424/485; 424/405; 424/420; 424/78.02; 424/78.03; 424/195.1; 514/787; 514/788.1; 514/789; 106/415; 106/504; 106/DIG. 3
[58] Field of Search .................................. 424/400, 401, 424/70.1, 70.6, 70.11, 70.12, 59, 405, 409, 417, 420, 421, 195.1, 196.1, 78.02, 78.03, 78.05–78.67; 106/415, 504, DIG. 3; 514/786, 787, 788.1, 789

[56] References Cited

U.S. PATENT DOCUMENTS

| 3,485,915 | 12/1969 | Gerstein et al. | 424/81 |
| 5,492,937 | 2/1996 | Bogentoft et al. | 514/781 |

FOREIGN PATENT DOCUMENTS

7228515  8/1995  Japan .

*Primary Examiner*—Neil S. Levy
*Attorney, Agent, or Firm*—Evelyn M. Sommer

[57] ABSTRACT

Described herein is a method for making a flake for use in a topical application. The flake is formed by contacting a liquid phase waxy material that may contain pigments, fragrance, plasticizer, hydrophilic modifier with a pseudoplastic hydrophilic gel, and/or an active ingredient. The waxy material contacts the surface of the gel and after the two materials have contacted, the waxy material is solidified and forms a sheet. This sheet is then broken into pieces to form the flakes of the present invention. The flakes can be used in formulating any topical product that can contain a lipid material.

18 Claims, 2 Drawing Sheets

DELIVERY SYSTEM FOR OIL SOLUBLE ACTIVES IN COSMETIC/PERSONAL CARE PRODUCTS

FIELD OF INVENTION

The present invention relates to a new means of delivering lipid soluble materials in cosmetic, pharmaceutical and personal care products. More particularly, the present invention relates to a means for delivering lipid soluble materials in a preparation designed for topical application. In some embodiments, the present invention adds a decorative and/or fragrance element to a topical preparation.

DESCRIPTION OF RELATED ART

Delivery of active ingredients to the top layers of the skin or stratum corneum has been a major focus of cosmetic and pharmaceutical manufacturers. Liposomes can deliver water soluble ingredients to the stratum corneum. These ingredients include water soluble vitamins such as ascorbic acid, or the B vitamins, Kojic acid, amino acids, and the like. See, for example, U.S. Pat. No. 5,279,834. Monolayer, bilayer and multi-lamellar liposomes have been employed as a method of encapsulating these water soluble active ingredients.

Bilayered and multi-lamellar phosphatidyl choline based liposomes are also capable of encapsulating lipophilic ingredients within the lipophilic zones of their structures. However, loading is difficult and the concentration of active ingredient is usually quite small.

The surfactants, emulsifiers and emollients normally found in cosmetic creams, lotions or ointments destabilize liposomes. Moreover, liposome production requires the use of costly, specialized equipment, has a slow rate of production, and uses expensive ingredients (95+% phosphatidyl choline). These factors limit the use of liposomes to special and/or expensive formulations.

A more cost effective method of delivering lipid soluble materials is microencapsulation. Microcapsules may be prepared using a variety of techniques and encapsulation materials (shells). The most commonly used encapsulation materials are cross linked gelatin, gelatin:acacia gum coacervates, ethyl cellulose, polyurethanes, epoxies and acrylics. Such microcapsules can be formed by a variety of different methods including simple and complex coacervation, in-situ ionic or covalent crosslinking, and spray-drying using Würster chambers (Glatt). Patents describing such methods include U.S. Pat. Nos. 3,623,489; 4,610,890; 4,830,773 and 5,093,182.

Gelatin is often employed as the encapsulating material in cosmetic applications. Gelatin is easily crosslinked with formaldehyde or glutaraldehyde to form structurally sound capsules. Unfortunately, these capsules do not rub well into the skin. Such capsules become more crosslinked, which over time results in a "plastic-like" shell that must be rinsed off the skin.

SUMMARY OF THE INVENTION

Briefly, the present invention includes a method for making a suspension including a lipid containing flake. This flake can be decorative and is useful for cosmetic, personal care, and pharmaceutical preparations.

The flake suspension is made from a pseudoplastic hydrophilic gel and a liquid phase waxy material. These materials are brought together at their respective surfaces. Desirably, as these materials are brought in contact, the waxy material is solidified. This solidified waxy material is then broken up into flakes, desirably of a small size.

The flakes of the present invention can incorporate lipid soluble active ingredients, coloring agents, fragrance or a combination thereof. The flakes are incorporated into conventional topical application product formulations, although such formulations may need to be modified to reflect the presence of a lipid soluble active ingredient in the flakes.

The flakes of the present invention deliver lipid soluble active ingredients, especially in preparations for topical use, much better than the delivery systems heretofore available. Moreover, this advantage is achieved without requiring a substantial investment in new or expensive equipment.

Additionally, the flakes of the present invention can add a decorative and/or fragrance element to the compositions in which they are employed. For example, in one embodiment of the present invention, flakes of more than one color are combined in a single product. The resulting product is reminiscent of confetti.

The present invention solves many of the problems that have been associated with decorative beads and flakes in personal care and cosmetic products. The expensive equipment previously required to produce beads and flakes is not needed using the formulations and techniques of the present invention. The present invention also allows incorporation of large amounts of oil-soluble active ingredients which play an important role in today's personal care products. The rub-in characteristics of the product of the present invention are superior to those of conventional decorative ingredients.

Moreover, as the flake matrix lowers the effective surface area to volume ratio, the present invention has the potential to increase the stability of labile ingredients such as vitamin A, vitamin C palmitate, vitamin E and other antioxidants, and other unstable oil soluble ingredients.

DETAILED DESCRIPTION OF THE INVENTION

A preferred process for preparing the lipophilic flakes of the present invention involves pumping a liquid phase waxy material, for example a molten wax, onto the surface of a pseudoplastic hydrophilic gel. In this process, it is further preferred that the gel is stirred to form a vortex during the step in which the waxy material is added to the surface of the pseudoplastic hydrophilic gel. Preferably, the vortex is formed by high shear mixing. As the liquid phase waxy material impinges upon the gel, desirably the waxy material is solidified. A preferred method of solidifying the waxy material when the waxy material is in the liquid phase as a molten wax is by cooling.

Figure 1:
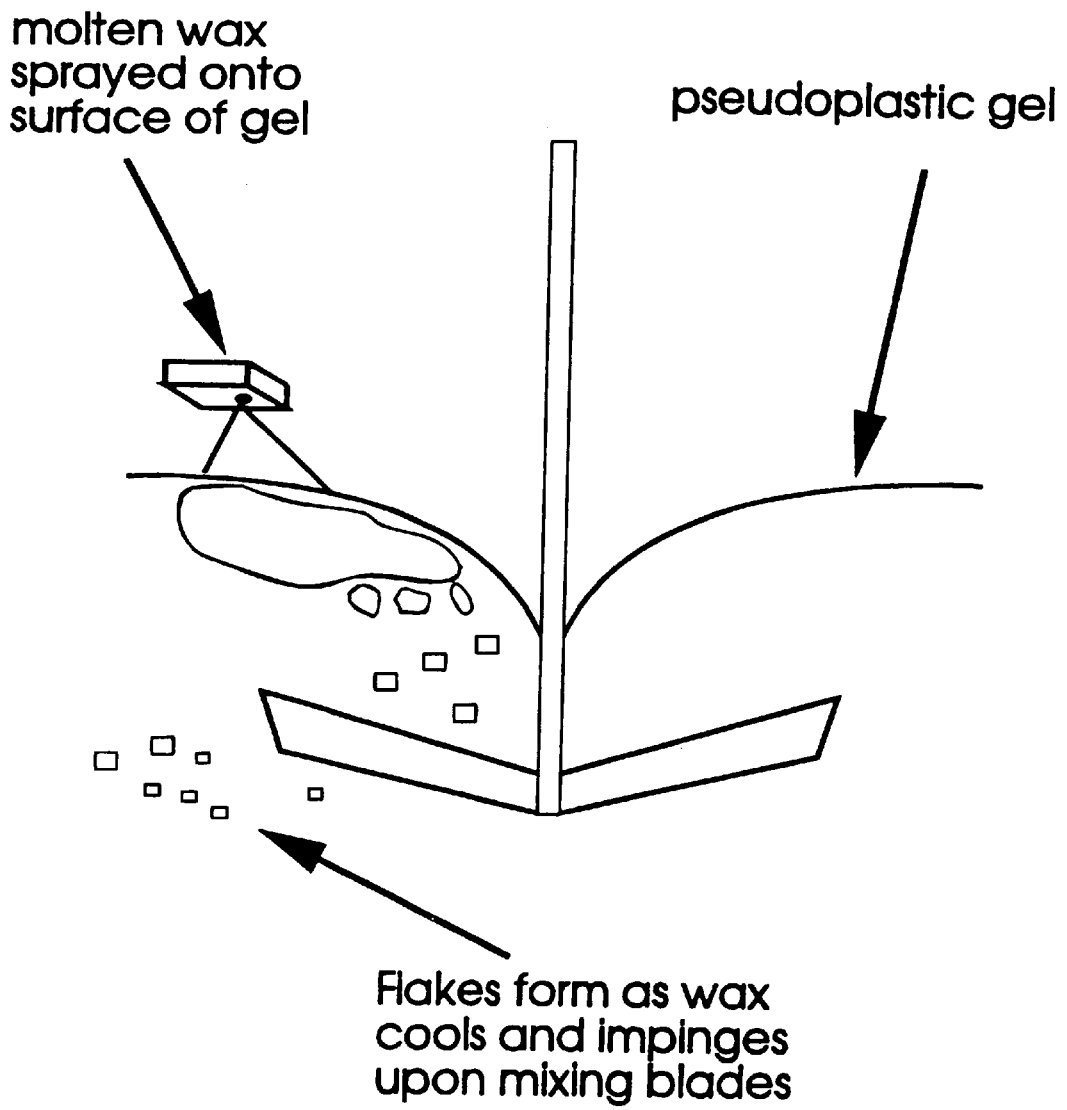
FIG. 1 illustrates a preferred embodiment of the process in which the flakes of the present invention are formed.
Figure 2:
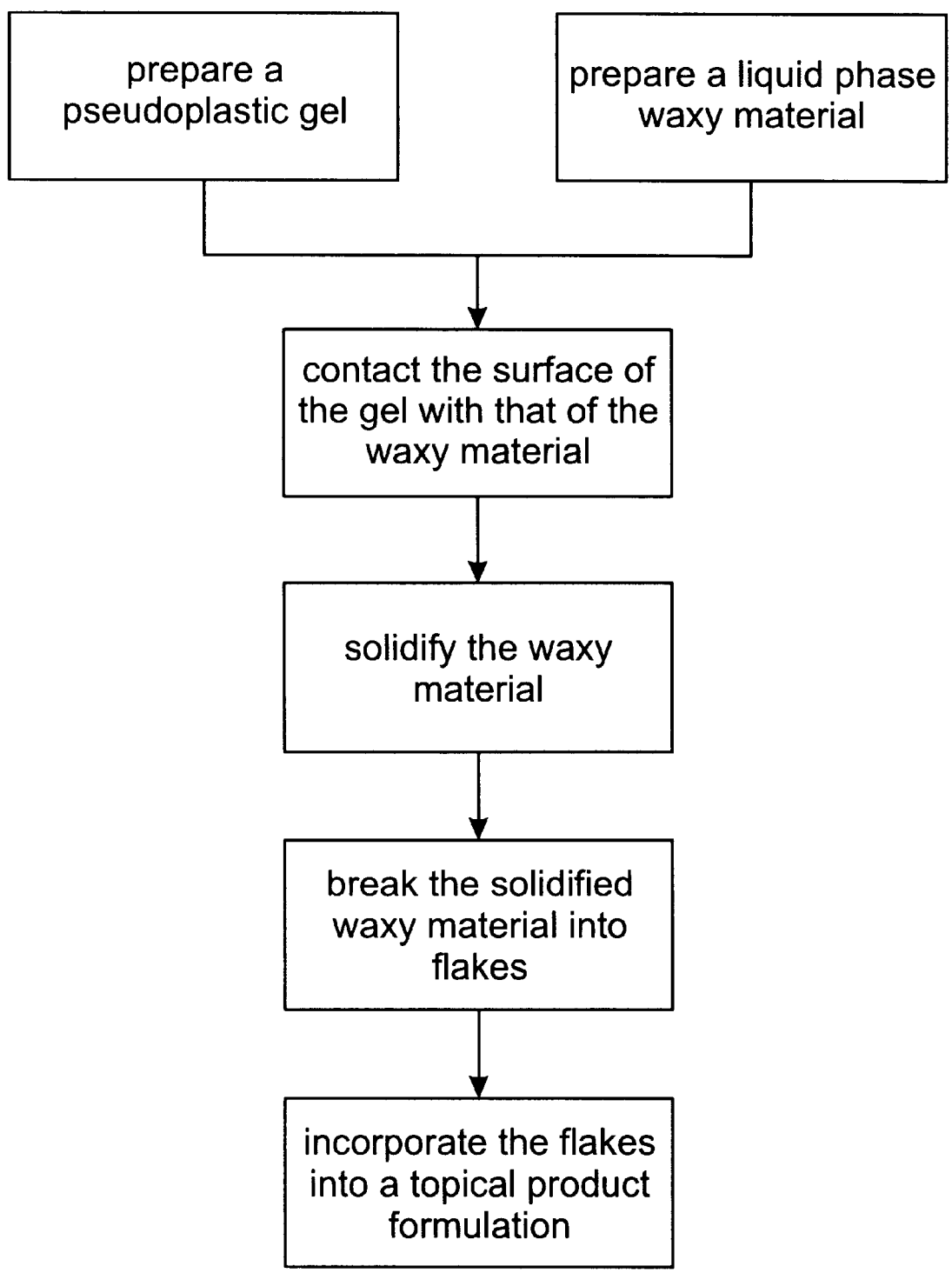
FIG. 2 shows a preferred embodiment of the process of the present invention.

The solidified sheet formed at the contact of the waxy material and the gel is, in a preferred embodiment, carried into the vortex of the mixing chamber. There the sheet is broken into small flakes (see FIG. 1). The dimension of these flakes is controlled by a number of factors which include the configuration of the mixing chamber, the mixing blade configuration and dimensions in relation to the mixing chamber, the gel rheological characteristics, the temperature and composition of the liquid phase waxy material and the mixing speed. For instance, as the velocity of the surface approaching the vortex increases, the flakes will be thinner. As the velocity of the gel at the tip of the blade increases, the flakes will be subjected to greater shear rates, and therefore become smaller. These parameters are alterable by changing gel characteristics, temperature, or other processing parameters.

Typically, the mixing chamber is cylindrical to facilitate the formation of a vortex. The mixing blade may be a standard propeller type or a turbo having 1/3 to 1/2 the diameter of the mixing chamber. The mixing speed will vary depending upon the preferred size of the flake and the rheology of the gel. A preferred flake size is about 3 to 30 mils (thousandths of an inch) thick with a surface of between about 1×1 mm to about 10×10 mm.

Unless noted otherwise, all measurements are by weight.

Any typical pseudoplastic hydrophilic gel such as Lubrajel (United-Guardian, Inc.), solutions of Stabileze (International Specialty Products), cellulose gums, cellulose gum esters, alginate gums, acrylic acid polymers, poly vinyl methyl ether/maleic anhydride (PVM/MA) decadiene crosspolymer, carbomer such as carbomer 940, hyaluronic acid or the like can be used in the process of the present invention. Useful cellulose gum esters include short chain (i.e., $C_1$–$C_6$) alkyl esters (such as the methyl, ethyl and propyl esters) as well as short chain (i.e., $C_1$–$C_6$) hydroxy alkyl esters. Gels with high pseudoplastic indices such as Lubrajel (glyceryl polymethacrylate) or Stabileze (PVM/MA decadiene crosspolymer), provide superior rheological characteristics for such in-situ flake formation.

The pseudoplastic gel may also contain a cationic gelling agent such as polyquaternium 1,2,3.

The gels used in the present invention are typically water based, desirably containing, on a total weight basis, between about 30 and 99.9 parts water, and more desirably between about 60 and 99.8 parts water. These gels can also include sodium hydroxide (desirably between about 0.005 and 0.1 parts), triethanolamine (desirably between about 0.02 and 2 parts), citric acid (desirably between about 0.02 and 2 parts), and an effective amount of a preservative. Preservatives useful in the gels used in the present invention include methyl and/or propyl paraben, imidazolidinyl urea, diazolidinyl urea, quaternium 15, or phenoxyethanol.

A preferred waxy material formulation is 40 parts Beeswax, 50 parts Vitamin E acetate (liquid form) and 10 parts of cosmetic grade Cloisonne Gold pearlescent pigment, such as that available from The Mearl Corporation. Typically, the waxy material includes between about and 99 percent of a wax type compound such as beeswax, fatty acid alcohols (desirably derived from intermediate chain fatty acids such as the about $C_{16}$ to about $C_{26}$ fatty acids including cetyl and stearyl), bayberry wax, rice bran wax, carnauba wax, microcrystalline waxes, ceresine wax, ozokerite wax, candelilla wax, sphingoceryl wax, montan wax, Japan wax, and spermaceti wax.

Additionally, the waxy material may comprise: a lipid soluble topically active ingredient, a pigment, silicone oils, fragrance, a plasticizer, and a hydrophilic modifier effective to enhance the rub-in characteristics of the flake.

Useful lipid soluble topically active ingredients include retinoic acid and dexamethasone; sunscreens such as octyl dimethyl PABA, octyl methoxycinnamate and oxybenzone; antipruritics such as corticosteroids; topical anesthetics such as Benzocaine, Dibucaine and Lidocaine; natural extracts such as eucalyptol; ginseng; lanolin; menthol; methyl salicylate; antifungals such as miconazole and clotrimazole; anti-dandruff medications such as coal tar extracts, selenium sulfide and zinc pyrithione; vitamins such as vitamin A, D, E and vitamin C lipophilic esters. Preferredly, such lipid soluble topically active ingredients comprise between about 0.5 and 50 percent of the waxy material.

Useful pigments include Cloissone Gold pigment (The Mearl Corporation), blue pigment (Cloissone Blue), silver-blue pigment (Duochrome Blue) and Flamenco Red. Preferredly, such pigments comprise between about 2 and 20 percent of the waxy material.

Useful silicone oils include cyclomethicone and dimethiconol. Preferably, such oils comprise between about 25 to 75 percent of the waxy material when the final product is to be a shampoo.

Useful fragrances include natural or synthetic oil soluble fragrances suitable for cosmetic applications. Preferredly, such fragrances comprise between about 0.05 and 50 percent of the waxy material.

Useful plasticizers include an application appropriate lipid soluble emollient, vegetable oil, mineral oil, petrolatum, oil soluble plant extracts and oil soluble vitamins. The ratio of plasticizer to wax is effective to provide cosmetically acceptable rub-in characteristics. A useful vegetable oil is peanut oil. Typically, the plasticizer constitutes between about 5 and 60 percent of the waxy material. Oil soluble vitamins useful as plasticizers in the present invention include Vitamin A, Vitamin C palmitate, Vitamin D, Vitamin E, and Vitamin K, and preferredly, the oil soluble vitamin is in a liquid form. Typically, when used, an oil soluble vitamin is present between about 5 and 50 percent of the waxy material.

When oil soluble vitamins are used as plasticizers, they also act as topically active ingredients.

Materials useful as hydrophilic modifiers which are effective to enhance the rub-in characteristics of the flake include ester or ether derivatives of PEG such as PEG-7 hydrogenated castor oil and PEG-4 lauryl ether. Typically, the hydrophilic modifiers comprise between about 2 and 20 percent of the waxy material.

It is preferred that all of the materials employed to make the waxy material used in the process of the present invention are homogeneously blended before they are incorporated into the process of making the present invention. Preferredly, the wax type compound is liquified by melting at a temperature of between about 45 and 70° C. In the liquid phase, the waxy material components are blended with moderate speed stirring.

The following examples illustrate the invention without limiting it thereto.

| Decorative Shower Gel Flakes | |
|---|---|
| Phase "A" | |
| Stearyl Alcohol | 50 parts |
| Petrolatum | 40 parts |
| Cloissone Gold pigment (The Mearl Corporation) | 10 parts |
| Phase "B" | |
| PVM/MA decadiene crosspolymer | 0.2 parts |
| Sodium hydroxide | 0.04 parts |
| Water | QS to 100 parts |
| Preservative | QS |

The phase "A" components are melted at about 55° C. and blended. Once blended, phase "A" is added slowly to phase "B" at a ratio of 1:20 (A:B). Concurrent with the addition of phase "A" to phase "B", the admixture is mixed at a high shear rate.

The flake suspension produced by this process is added to a conventional shower gel formulation at a use concentration of between about 4 and 8 percent (by weight) of the total gel formulation.

| Vitamin A and E fortified Cosmetic Flakes | |
|---|---|
| Phase "A" | |
| Synthetic Beeswax | 40 parts |
| Petrolatum | 10 parts |
| Vitamin E Acetate (oil) | 20 parts |
| Vitamin A Palmitate | 20 parts |
| Blue pigment | 10 parts |
| Phase "B" | |
| Carbomer 940 | 0.4 parts |
| Triethanolamine | 0.2 parts |
| Water | QS to 100 parts |
| Preservative | QS |

The phase "A" components are melted at about 50° C. and blended. Once blended, phase "A" is added slowly to phase "B" at a ratio of 1:20 (A:B). Concurrent with the addition of phase "A" to phase "B", the admixture is mixed at a high shear rate.

The flake suspension of this example is incorporated into a conventional, clear, water-based cosmetic gel. Typical use concentration is between about 3 and 6 percent. This preparation should deliver Vitamin A and E in a clear water-based product.

| Alcohol-free Fragrance Bursting Flake | |
|---|---|
| Phase "A" | |
| Candelilla wax | 10 parts |
| Rice Bran Wax | 10 parts |
| Spermaceti wax | 20 parts |
| Fragrance compound | 40 parts |
| Vitamin C Palmitate | 10 parts |
| Silver-blue pigment | 10 parts |
| Phase "B" | |
| Glyceryl polymethacrylate (Lubrajel DV) | 30 parts |
| Water | 70 parts |
| Preservative | QS |

The phase "A" components are melted at about 55° C. and blended. Once blended, phase "A" is added slowly to phase "B" at a ratio of 1:20 (A:B). Concurrent with the addition of phase "A" to phase "B", the admixture is mixed at a high shear rate.

The flake suspension of this example is incorporated into a conventional, clear, water-based cosmetic gel. Typical use level is in such a gel is between about 3 and 5 percent. Upon application to the skin, this alcohol-free system should deliver a burst of fragrance.

| Retin-A Topical Acne Gel | |
|---|---|
| Phase "A" | |
| Bayberry wax | 20 parts |
| Ozokerite wax | 20 parts |
| Cetyl alcohol | 75 parts |
| Sphingoceryl wax | 20 parts |
| Petrolatum | 30 parts |
| Retinoic Acid | 2.5 parts |
| Phase "B" | |
| Hydroxypropyl methylcellulose | 1.75 parts |
| Sodium hydroxide | 0.01 parts |
| Citric acid | 0.02 parts |
| Water | QS to 100 parts |
| Preservative | QS |

The phase "A" components are melted at about 65° C. and blended. Once blended, phase "A" is added slowly to phase "B". Concurrent with the addition of phase "A" to phase "B", the admixture is mixed at a high shear rate.

This flake suspension is incorporated into a conventional, clear, water-based cosmetic gel at a level effective to provide 0.01% (by weight) retinoic acid.

| 2-in-1 Hair Conditioning Shampoo | |
|---|---|
| Phase "A" | |
| Stearyl Alcohol | 25 parts |
| Beeswax | 25 parts |
| Cyclomethicone and dimethiconol | 50 parts |
| Phase "B" | |
| Hydroxypropyl methylcellulose | 1.75 parts |
| Sodium hydroxide | 0.01 parts |
| Citric acid | 0.02 parts |
| Water | QS to 100 parts |
| Preservative | QS |

The phase "A" components are melted at about 55° C. and blended. Once blended, phase "A" is added slowly to phase "B" at a ratio of 1:15 (A:B). Concurrent with the addition of phase "A" to phase "B", the admixture is mixed at a high shear rate.

The flake suspension is then incorporated into a conventional shampoo formulation at a concentration of between 5 and 10 percent. As the flakes are rubbed into the hair, it is believed that the cyclomethicone and dimethiconol are released and which should provide conditioning and shine to the treated hair.

| Dexamethasone Dermatitis Treatment Gel | |
|---|---|
| Phase "A" | |
| Stearyl Alcohol | 50 parts |
| Dexamethasone | 2 parts |
| Peanut Oil | 45 parts |
| PEG-7 Hydrogenated Castor Oil | 3 parts |
| Phase "B" | |
| Hydroxypropyl methylcellulose | 1.75 parts |
| Sodium hydroxide | 0.01 parts |
| Citric acid | 0.02 parts |
| Water | QS to 100 parts |
| Preservative | QS |

The phase "A" components are melted at about 55° C. and blended. Once blended, phase "A" is added slowly to phase "B" at a ratio of 1:15 (A:B). Concurrent with the addition of phase "A" to phase "B", the admixture is mixed at a high shear rate.

The flake suspension is then incorporated into a carbomer gel at 5 percent. The final topical drug product contains 0.1% dexamethasone and is believed to be suited for the treatment of dermatitis, eczema, psoriasis and other pruritic conditions.

What I claim is:

1. A method of forming flakes for use in a topical skin preparation comprising:
   a. preparing a pseudoplastic hydrophilic gel;
   b. preparing a liquid phase of a lipophilic solid with plastic rheology;
   c. contacting a surface of said pseudoplastic hydrophilic gel with a surface of said liquid phase of a lipophilic solid with plastic rheology;
   d. solidifying said liquid phase of a lipophilic solid with plastic rheology after it has contacted said pseudoplastic hydrophilic gel; and
   e. breaking said solidified of a lipophilic solid with plastic rheology into small pieces.

2. The method of claim 1 wherein said lipophilic solid with plastic rheology includes a plasticizer selected from the group consisting of: a lipid soluble emollient, vegetable oil, mineral oil, petrolatum, oil soluble plant extract and oil soluble vitamins.

3. The method of claim 2 wherein said oil soluble vitamin is selected from the group consisting of Vitamin A, Vitamin C palmitate, Vitamin D, Vitamin E, and Vitamin K.

4. The method of claim 2 wherein said lipophilic solid with plastic rheology includes a lipid-soluble, non-vitamin, active ingredient selected from the group consisting of retinoic acid, octyl dimethyl p-aminobenzoic acid, octyl methoxycinnamate, oxybenzone, antipruritics, topical anesthetics, eucalyptol, ginseng, lanolin, menthol, methyl salicylate, antifungals, coal tar extracts, selenium sulfide and zinc pyrithione.

5. The method of claim 2 wherein said lipid soluble emollient includes a fatty acid ester.

6. The method of claim 1 in which said solidifying step includes cooling the lipophilic solid with plastic rheology.

7. The method of claim 6 in which said breaking step includes impinging said solidified lipophilic solid with plastic rheology upon a high shear mixing blade.

8. The method of claim 1 in which said pseudoplastic hydrophilic gel includes at least one member of the group consisting of carbomer, glyceryl polymethacrylate, cellulose gum, poly vinyl methyl ether/maleic anhydride decadiene cross polymer cellulose gum ethers, hyaluronic acid, and cationic gelling agents.

9. The method of claim 8 in which said cellulose gum ethers include at least one of the methyl, ethyl and propyl ethers.

10. The flake suspension prepared by the method of claim 1.

11. The method of claim 1 in which said lipophilic solid with plastic rheology consists essentially of at least one wax selected from the group consisting of beeswax, bayberry, rice bran wax, carnauba, microcrystalline waxes, ceresine, ozokerite, candelilla, sphingoceryl, montan wax, Japan wax and spermaceti wax.

12. The flake suspension of claim 10 which contains a second flake suspension, said second flake suspension containing a pseudoplastic gel, lipophilic solid with plastic rheology and a pigment different from the pigment of the first flake suspension.

13. The method of claim 1 in which said lipophilic solid with plastic rheology includes a fatty alcohol.

14. The method of claim 13 in which said fatty alcohol includes an intermediate chain length fatty alcohol.

15. The method of claim 1 in which said lipophilic solid with plastic rheology includes a hydrophilic modifier effective to enhance the rub-in characteristics of the flake.

16. The method of claim 15 in which said hydrophilic modifier effective to enhance the rub-in characteristics of the flake includes a member of the group consisting of polyethylene glycol (PEG) esters and PEG ethers.

17. The method of claim 15 in which said hydrophilic modifier effective to enhance the rub-in characteristics of the flake includes a member of the group consisting of PEG-7 hydrogenated castor oil and PEG-4 lauryl ether.

18. A 2-in-1 shampoo including a decorative flake suspension comprising
   i) a pseudoplastic gel;
   ii) a lipophilic solid with plastic rheology including at least one silicone oil; and
   iii) a pigment.

* * * * *